United States Patent
Kim et al.

(10) Patent No.: US 8,442,613 B2
(45) Date of Patent: May 14, 2013

(54) MAPPING PROBE ASSEMBLY WITH SKIVED TUBE BODY FRAME

(75) Inventors: Isaac Kim, San Jose, CA (US); Josef Koblish, Sunnyvale, CA (US)

(73) Assignee: Boston Scientific Scimed, Inc, Maple Grove, MN (US)

( * ) Notice: Subject to any disclaimer, the term of this patent is extended or adjusted under 35 U.S.C. 154(b) by 279 days.

(21) Appl. No.: 12/840,441

(22) Filed: Jul. 21, 2010

(65) Prior Publication Data
US 2011/0028826 A1     Feb. 3, 2011

Related U.S. Application Data

(60) Provisional application No. 61/229,646, filed on Jul. 29, 2009.

(51) Int. Cl.
*A61B 5/042*     (2006.01)
(52) U.S. Cl.
USPC .......................................... 600/374; 600/381
(58) Field of Classification Search .................. 600/374, 600/381; 606/41
See application file for complete search history.

(56) References Cited

U.S. PATENT DOCUMENTS

| | | | |
|---|---|---|---|
| 5,154,387 A | 10/1992 | Trailer | |
| 5,919,188 A | 7/1999 | Shearon et al. | |
| 6,569,162 B2 | 5/2003 | He | |
| 6,602,242 B1 | 8/2003 | Fung et al. | |
| 6,640,120 B1 | 10/2003 | Swanson et al. | |
| 6,671,533 B2 * | 12/2003 | Chen et al. | 600/374 |
| 6,689,128 B2 | 2/2004 | Sliwa, Jr. et al. | |
| 6,702,811 B2 * | 3/2004 | Stewart et al. | 606/41 |
| 6,795,721 B2 * | 9/2004 | Coleman et al. | 600/374 |
| 6,804,545 B2 | 10/2004 | Fuimaono et al. | |
| 6,805,128 B1 | 10/2004 | Pless et al. | |
| 7,278,993 B2 | 10/2007 | Kelly et al. | |
| 7,387,126 B2 | 6/2008 | Cox et al. | |

(Continued)

FOREIGN PATENT DOCUMENTS

| | | |
|---|---|---|
| EP | 1690510 A1 | 8/2006 |
| WO | WO-2008/118992 A1 | 10/2008 |

(Continued)

OTHER PUBLICATIONS

"International Application Serial No. PCT/US2010/039600, Invitation to Pay Additional Fee mailed Aug. 30, 2010", 6 pgs.

(Continued)

*Primary Examiner* — Lee S Cohen
(74) *Attorney, Agent, or Firm* — Seager, Tufte & Wickhem, LLC

(57) ABSTRACT

An embodiment of a mapping probe assembly includes a body frame with a lumen therein. The body frame includes a catheter shaft region, a loop section and a transition region between the catheter shaft region and a loop section. A plurality of mapping electrodes are attached around the loop section. Electrical conductors extend through the lumen of the body frame to the mapping electrodes. In some embodiments, the loop section is skived, where a portion of the body frame is removed toward the interior of the loop section. The loop section has a generally planar loop, and further has a loop center. In some embodiments, the catheter shaft has an alignment generally perpendicular to the loop section where the alignment of the catheter shaft is along a line that intersects the planar loop proximate to the loop center.

22 Claims, 6 Drawing Sheets

U.S. PATENT DOCUMENTS

| | | |
|---|---|---|
| 8,221,409 B2 | 7/2012 | Cao et al. |
| 2002/0107511 A1 | 8/2002 | Collins et al. |
| 2003/0004506 A1 | 1/2003 | Messing |
| 2004/0092806 A1 | 5/2004 | Sagon et al. |
| 2005/0070894 A1 | 3/2005 | McClurken |
| 2008/0243214 A1 | 10/2008 | Koblish |
| 2008/0300454 A1 | 12/2008 | Goto |
| 2009/0093810 A1 | 4/2009 | Subramaniam et al. |
| 2010/0331658 A1 | 12/2010 | Kim et al. |
| 2011/0009857 A1 | 1/2011 | Subramaniam et al. |
| 2011/0022041 A1 | 1/2011 | Ingle et al. |

FOREIGN PATENT DOCUMENTS

| | | |
|---|---|---|
| WO | WO-2009/048824 A1 | 4/2009 |
| WO | WO-2009/048943 A1 | 4/2009 |
| WO | WO-2011/008444 A1 | 1/2011 |
| WO | WO-2011/008681 A1 | 1/2011 |

OTHER PUBLICATIONS

"International Application Serial No. PCT/US2010/039600, International Search Report mailed Nov. 10, 2010", 5 pgs.

"International Application Serial No. PCT/US2010/039600, Written Opinion mailed Nov. 10, 2010", 8 pgs.

"International Application Serial No. PCT/US2010/041677, International Search Report mailed Aug. 20, 2010", 4 pgs.

"International Application Serial No. PCT/US2010/041677, Written Opinion mailed Aug. 20, 2010", 6 pgs.

Ingle, Frank, et al., "Systems and Methods for Titrating RF Ablation", U.S. Appl. No. 12/835,367, filed Jul. 13, 2010.

Kim, Isaac, et al., "Map and Ablate Open Irrigated Hybrid Catheter", U.S. Appl. No. 12/821,459, filed Jun. 23, 2010.

Subramaniam, Raj, et al., "Open-Irrigated Ablation Catheter with Turbulent Flow", U.S. Appl. No. 12/834,265, filed Jul. 12, 2010.

* cited by examiner

MAPPING PROBE ASSEMBLY WITH SKIVED TUBE BODY FRAME

CROSS REFERENCE TO RELATED APPLICATION

This application claims the benefit of U.S. Provisional Application No. 61/229,646, filed on Jul. 29, 2009, under 35 U.S.C. §119(e), which is hereby incorporated by reference in its entirety.

TECHNICAL FIELD

This application relates generally to medical devices and, more particularly, to mapping probe assemblies.

BACKGROUND

Aberrant conductive pathways can develop in heart tissue and the surrounding tissue, disrupting the normal path of the heart's electrical impulses. For example, conduction blocks can cause the electrical impulse to degenerate into several circular wavelets that disrupt the normal activation of the atria or ventricles. The aberrant conductive pathways create abnormal, irregular, and sometimes life-threatening heart rhythms called arrhythmias.

Ablation is one way of treating arrhythmias and restoring normal contraction. One ablation technique is radio frequency (RF) ablation. The sources of the aberrant pathways, referred to as focal arrhythmia substrates, are located and then destroyed or ablated. Extra electrical pathways, which may trigger an atrial arrhythmia, may be formed at the base or within one or more pulmonary veins. To treat such an aberration, physicians may use multiple catheters to gain access into interior regions of the pulmonary vein tissue for mapping and ablating targeted tissue areas. The process is referred to as pulmonary vein (PV) isolation. A mapping catheter can be used to map the aberrant conductive pathway within the pulmonary vein. A physician introduces the mapping catheter through a main vein, typically the femoral vein, and into the interior region of the pulmonary vein that is to be treated. The antrum or the ostium of the PV is mapped at the beginning of the procedure. Based on this electrical mapping potential foci for the arrhythmia are identified.

An introducer guide sheath or guide wire may be used to place the mapping catheter within the vasculature of the patient. The introducer guide sheath is introduced into the left atrium of the heart using a conventional retrograde approach, i.e., through the respective aortic and mitral valves of the heart. Alternatively, the introducer guide sheath may be introduced into the left atrium using a transeptal approach, i.e., through the atrial septum. In either method, the catheter is introduced through the introducer guide sheath until a probe assembly at a distal portion of the catheter resides within the left atrium. Once inside the left atrium, the physician may deliver the probe assembly into a desired pulmonary vein using a steering mechanism. The physician situates the probe assembly within a selected tissue region in the interior of the pulmonary vein, adjacent to the opening into the left atrium, and maps electrical activity in the pulmonary vein tissue using one or more electrodes of the probe assembly. After mapping, the physician may introduce an ablation catheter to ablate the aberrant tissue using an ablation electrode carried on the distal tip of the ablation catheter to the interior of the pulmonary vein. The ablation electrode is placed in direct contact with the tissue that is to be ablated. The physician directs RF energy from the ablation electrode through tissue to ablate the tissue and form a lesion.

FIGS. 1A-1B illustrate a known mapping catheter with a catheter body 101 generally tangential to a loop-shaped probe assembly 102 and orthogonal to a loop plane 103 for the loop-shaped probe assembly 102. This design is relatively small. The probe assembly is a generally tubular structure, which is formed into the loop shape for the probe assembly. The diameter of the tubular structure is on the order of 3½ Fr (1.2 mm). However, this design provides challenges for maintaining a stable orientation to perform the mapping.

SUMMARY

An embodiment of a mapping probe assembly includes a body frame with a lumen therein. The body frame includes a catheter shaft region and a skived loop section where a portion of the body frame is removed toward the interior of the skived loop section. A plurality of mapping electrodes are attached around the skived loop section. Electrical conductors extend through the lumen of the body frame to the mapping electrodes.

An embodiment of a mapping probe assembly includes a body frame with a lumen therein. The body frame includes a catheter shaft region, a loop section, and a transition region between the catheter shaft region and the loop section. The loop section has a generally planar loop, and further has a loop center. The catheter shaft has an alignment generally perpendicular to the loop section where the alignment of the catheter shaft is along a line that intersects the planar loop proximate to the loop center. A plurality of mapping electrodes are attached around the loop section. Electrical conductors extend through the lumen of the body frame to the mapping electrodes.

An embodiment of a mapping system includes a steerable catheter with the distal end and a sheath at the end, and further includes a mapping probe assembly configured to be deployed through the distal end of the steerable catheter and to collapse into the sheath of the steerable catheter. The mapping probe assembly includes a body frame with a lumen therein. The body frame includes a catheter shaft region and a skived loop section where a portion of the body frame is removed toward the interior of the skived loop section. In the deployed mapping probe assembly, the skived loop section has a generally planar loop and a loop center, and the catheter shaft has an alignment generally perpendicular to the loop section. The alignment of the catheter shaft is along a line that intersects the planar loop proximate to the loop center. A plurality of mapping electrodes are attached around the skived loop section. Electrical conductors extend through the lumen of the body frame to the mapping electrodes.

This Summary is an overview of some of the teachings of the present application and not intended to be an exclusive or exhaustive treatment of the present subject matter. Further details about the present subject matter are found in the detailed description and appended claims. The scope of the present invention is defined by the appended claims and their equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

The following detailed description of the present invention refers to subject matter in the accompanying drawings which show, by way of illustration, specific aspects and embodiments in which the present subject matter may be practiced. These embodiments are described in sufficient detail to enable those skilled in the art to practice the present subject matter. References to "an," "one" or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Embodiments of the present subject matter relate to a PV mapping catheter configuration that allows the catheter to be positioned properly in the PV ostium. The design encourages the set position of the catheter to be maintained throughout the ablative procedure. The mapping loop tip is formed from a material with a shape memory, which tends to expand radially outward into contact with the interior walls of the PV ostium. The mapping loop may be designed for vessels other than the PV ostium. The catheter shaft is generally centered in relation to the mapping loop tip, which allows the catheter distal loop force pressure upon the PV ostium to be distributed in a generally uniform manner about its circumference which is in contact with the interior wall of the PV ostium. This uniformly-distributed pressure maintains a more balanced orientation and stable position of the original deployment, which improves mapping of the heart atrium or ostium of the PV before and after the ablative therapy. According to various embodiments, the loop tip includes ablation electrodes. Some embodiments use electrodes for the mapping function that are different than the electrodes used to perform the RF ablation. Some embodiments use the same electrodes to map and to ablate.

Figure 1A:
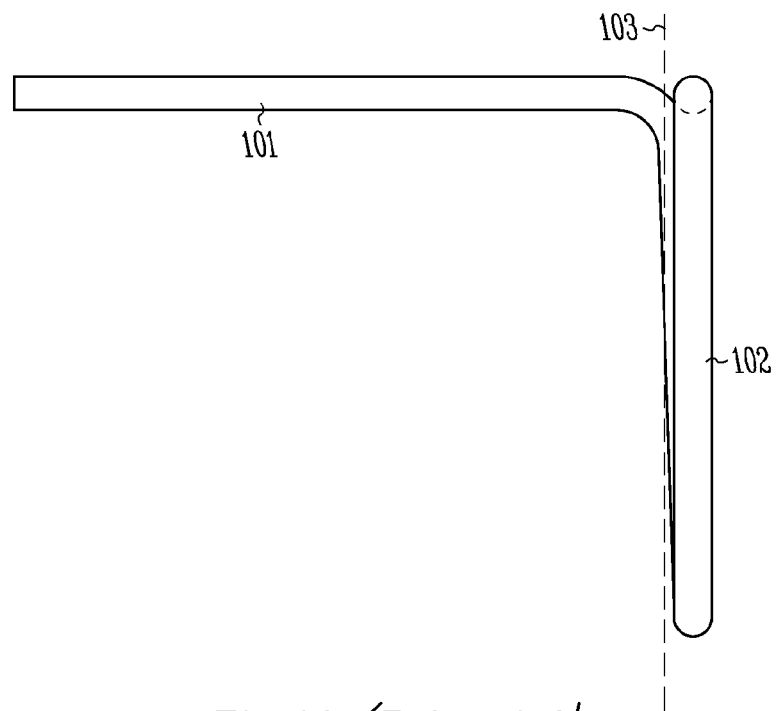
FIGS. 1A-1B illustrate a known mapping catheter with a catheter body generally tangential and orthogonal to a loop-shaped probe assembly.
Figure 1B:
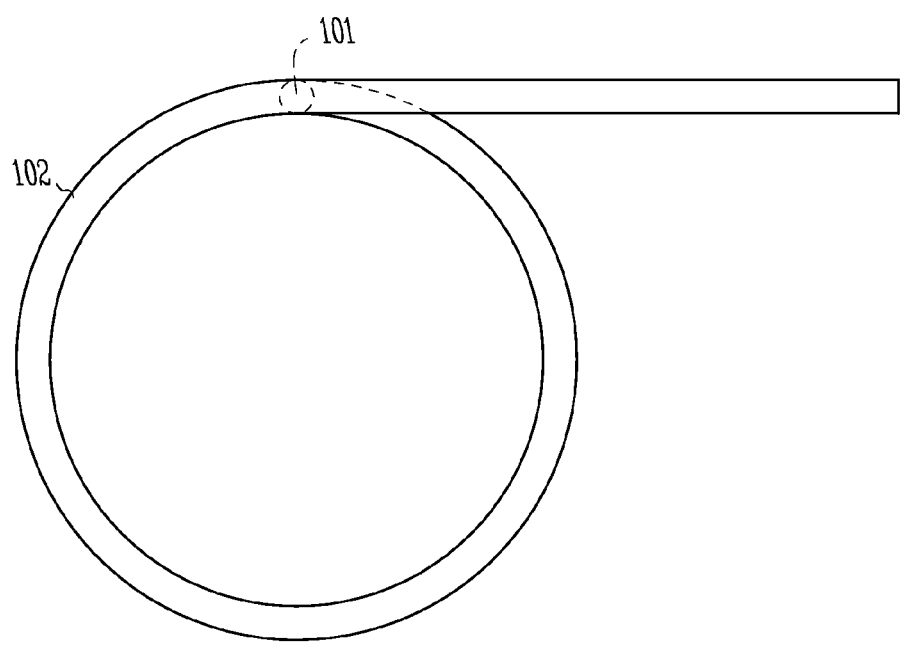
Figure 2:
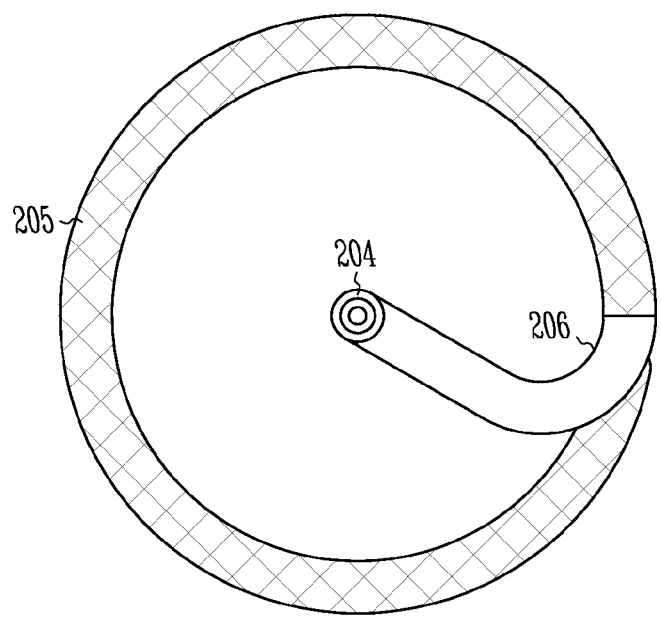
FIG. 2 illustrates a plan view for an embodiment of a probe assembly for a mapping catheter.

FIG. 2 illustrates a plan view for an embodiment of a probe assembly for a mapping catheter. The illustrated mapping catheter has a distal region of a catheter shaft 204, and a generally planar and circular mapping loop tip 205. The distal region of the catheter shaft 204 extends away from the page in the illustrated plan view, and is generally perpendicular to the plane of the mapping loop 205. The loop 205 is formed with a desired loop diameter to fit within a desired vessel, such as the PV ostium, and securely expand into contact with the interior wall of the vessel. The diameter of the loop is adjustable. The shape memory of the material used to form the mapping loop tip tends to enlarge the diameter of the mapping loop, and a control wire can be used to adjust the diameter. In an embodiment of a PV mapping catheter, the diameter of the loop is approximately 10-30 mm. The length of a mapping catheter embodiment is within a range of approximately 100 cm to 150 cm. The diameter of the catheter is within the range of 5 to 9 Fr (1.2 to 3 mm), according to some embodiments. Some catheter embodiments have a diameter within the range of 6 to 8 Fr (2 to 2.7 mm). In some embodiments, the catheter diameter is on the order of 7 Fr (2.3 mm). The diameter of the structure that defines the mapping loop tip is within the range of 2 to 9 Fr (0.7 to 3 mm), according to various embodiments. In some embodiments, the diameter of the structure that defines the mapping loop tip is 2 to 5 Fr (0.7 to 1.7 mm). In some embodiments, the diameter of this structure is on the order of 3½ Fr (1.2 mm). The illustrated catheter includes a transition region 206 between the distal region of the catheter shaft 204 and the mapping loop 205. The distal region of the catheter shaft 204 is generally aligned with an axis of rotation of the generally circular mapping loop 204. Thus, in the plan view illustrated in FIG. 2, the catheter shaft is generally centered with respect to the mapping loop 205. The distal region of the catheter shaft 204, the transition region 206 and the mapping loop 205 possess a shape memory to return to a shape generally illustrated in FIG. 2, but also possess flexibility to be straightened when retracted in a sheath. As will be illustrated in the figures below, the distal portion of the catheter includes a body frame, a control or pull wire, a compression spring for the adjustable loop, a distal braided shaft, and outer shaft with electrodes attached.

Figure 3:
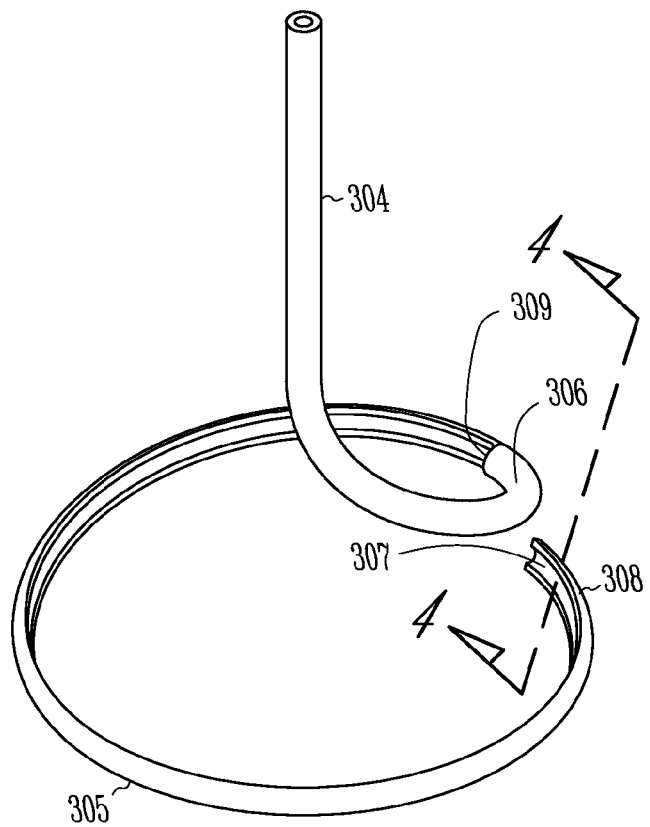
FIG. 3 illustrates a perspective view of a body frame for an embodiment of a distal portion of a probe assembly for a mapping catheter.

FIG. 3 illustrates a perspective view of a body frame for an embodiment of a distal portion of a probe assembly for a mapping catheter. Embodiments of the present subject matter use a body frame made of Nickel Titanium (NiTi) to provide shape memory. Other materials that possess an appropriate shape memory may be used. Because of the shape memory characteristic, the distal portion of the catheter is flexible and can be straightened inside the sheath and can maintain its original shape when is out of the sheath. According to various embodiments the loop section of the body frame is skived. In the skived portion, at least a portion of the body frame facing toward the interior of the loop is removed. The skived structure allows the design to accommodate more space for the lead wires, provides a small outside diameter profile, provides balanced distal loop flexibility, and provides a more controlled, adjustable loop. Some embodiments taper the skived portion distally. The tapered distal end promotes flexibility of the distal end of the loop portion, which allows the mapping loop to be fed through the vascular more easily and to contract into a tighter loop. In the tapered embodiments, the amount of the body frame left at the proximal end of the skived portion is more than the amount of the body frame left at the distal end. For example, the skive may leave approximately half of the body frame in the skived portion, and this portion is tapered to leave approximately half of the body frame at the proximal end and approximately a quarter of the body frame at the distal end. Various embodiments leave different amounts of the body frame at the distal end and different amounts of the body frame at the proximal end. The skiving and tapering is a design parameter that can be modified to provide the desired flexibility for the mapping loop, and to provide the desired thickness for the structure used to define the mapping loop.

Figure 4:
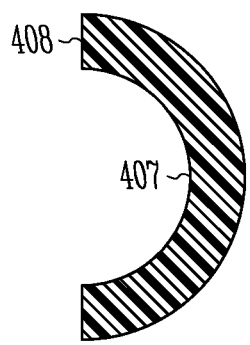
FIG. 4 illustrates a cross-sectional view taken along lines 4-4 in FIG. 3A of the body frame.

The body frame is a tubular structure with a lumen therein. The body frame includes a catheter shaft region 304, a loop section 305, a transition region between the catheter shaft region 304 and the loop section 305, and a compression spring 309 positioned between the skived loop section and the transition region 306. The loop section 305 of the body frame is skived to remove the interior portion of the loop, thereby exposing the lumen 307 and a cross section of a wall 308 of the tubular structure that defines the lumen within the tubular structure. FIG. 4 illustrates a cross-sectional view taken along lines 4-4 in FIG. 3 of the body frame. This figure generally illustrates the partial tubular shape of the skived loop section, the lumen 407 and the wall of the tubular structure 408 used to form the body frame.

Figure 5:
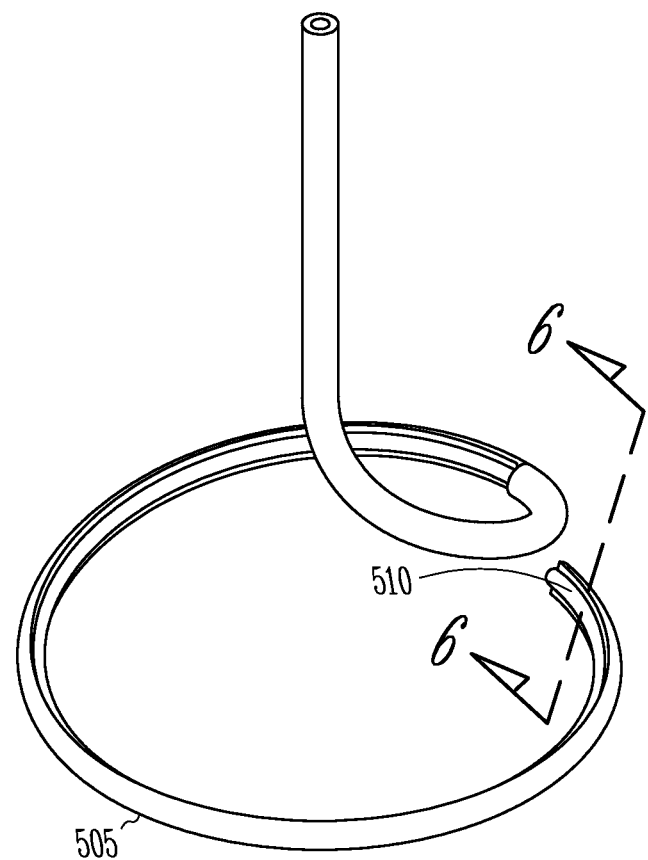
FIG. 5 illustrates a perspective view of the body frame illustrated in FIG. 3A, with a control wire therein, according to various embodiments.
Figure 6:
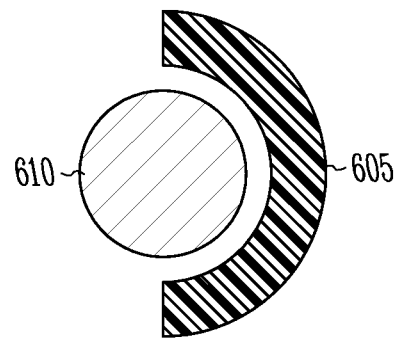
FIG. 6 illustrates a cross-sectional view taken along lines 6-6 in FIG. 5 of the body frame.

FIG. 5 illustrates a perspective view of the body frame illustrated in FIG. 3A, with a control wire 510 therein, according to various embodiments. The control or pull wire may be 10 mm, 8 mm or 7 mm, according to various embodiments. The present subject matter is not limited to a particular size. The control wire is attached to the body frame toward the distal end of the loop section 505. Pushing the control wire distally tends to straighten the body frame thereby making the loop larger, and pulling the control wire proximally tends to make the loop smaller. FIG. 6 illustrates a cross-sectional view taken along lines 6-6 in FIG. 5 of the body frame. This figure generally illustrates the control wire 610 within the exposed lumen of the skived loop section 605.

Figure 7:
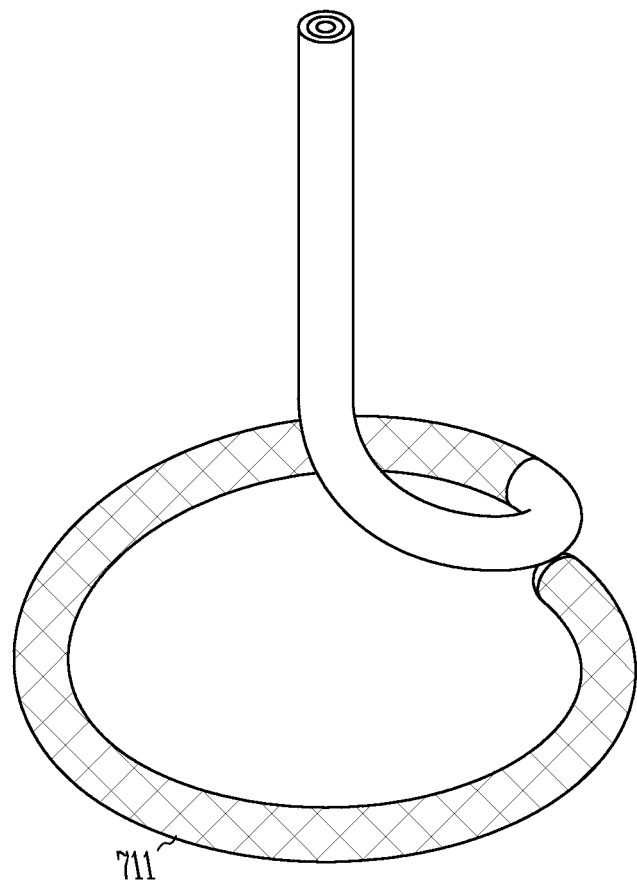
FIG. 7 illustrates a distal braided shaft incorporated on the distal end of the body frame, according to various embodiments.

FIG. 7 illustrates a distal braided shaft incorporated on the distal end of the body frame, according to various embodiments. The distal braided shaft extends substantially around the loop. In some embodiments, the braid 711 is a stainless steel wire. Some embodiments form the braid using nylon, fiberglass or other thermoplastic material. The braid provides structural reinforcement to the structure of the loop, preventing the wires within the structure from rupturing the loop structure.

Figure 8:
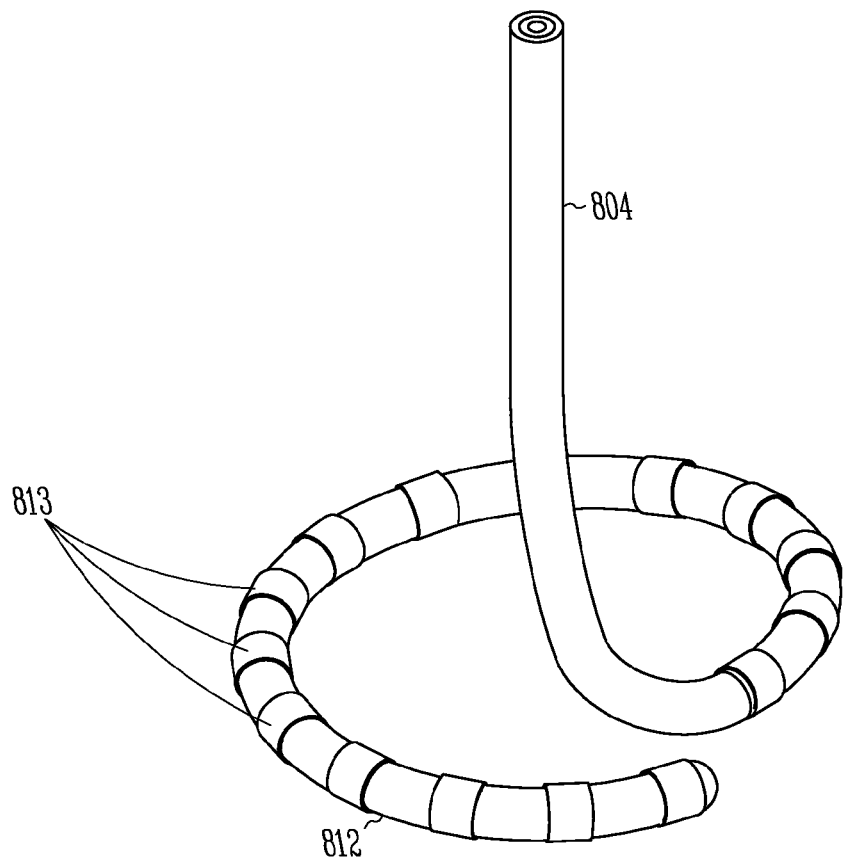
FIG. 8 illustrates an outer shaft, with electrodes, incorporated over the braids on the distal end of the body frame.

FIG. 8 illustrates an outer shaft 812, with electrodes 813, incorporated over the braids on the distal end of the body frame. The outer shaft 812 may be formed from a thermoplastic material. Holes are formed through the outer shaft. Ring electrodes are connected around the outer shaft. Wires within the catheter and loop section connect to the electrodes through these holes. According to various embodiments, the electrodes are equally spaced around the loop. In some embodiments, the number of electrodes around the loop is within a range from approximately 10 to 30 electrodes. By way of example and not limitation, some embodiments provide approximately 22 ring electrodes. In some embodiments, by way of example and not limitation, the length of the electrodes is approximately 1-2 mm, and the spacing between electrodes is approximately 6 mm. The length of electrodes, the spacing of electrodes, and the number of electrodes on the mapping loop may be varied.

Figure 9A:
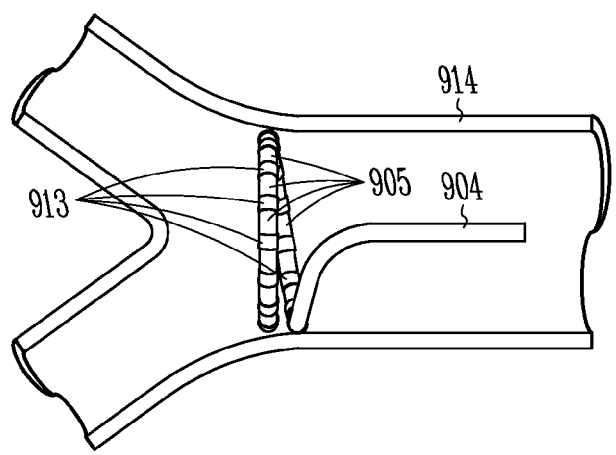
FIGS. 9A and 9B illustrate an embodiment of a probe assembly of a mapping catheter positioned within a pulmonary vein.
Figure 9B:
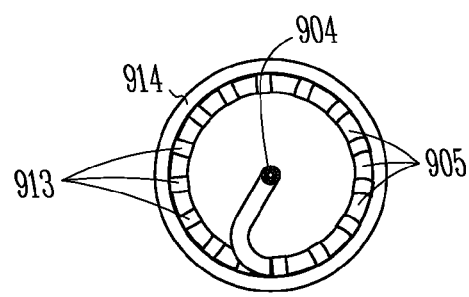

FIGS. 9A and 9B illustrate an embodiment of a probe assembly of a mapping catheter positioned within a pulmonary vein. The mapping catheter may be positioned within the PV ostium. As illustrated, the loop section 905 expands into contact with the interior wall of the pulmonary vein 914, and the distal portion of the catheter shaft 904 is approximately centered within the pulmonary vein, as it is generally aligned with the axis of rotation of the loop section 905. This design enables the loop section 905 to expand against the wall of the pulmonary vein with a general uniform pressure. The area of the loop section in contact with the wall of the pulmonary vein is generally uniform around the diameter of the pulmonary vein, and the distal portion of the catheter shaft does not tend to pull one portion of the loop section away from the wall of the pulmonary vein, as would occur if the catheter shaft was tangential to the loop section. This allows the catheter to be securely positioned and provide a stable orientation for the mapping electrodes 913 throughout the procedure.

Figure 10:
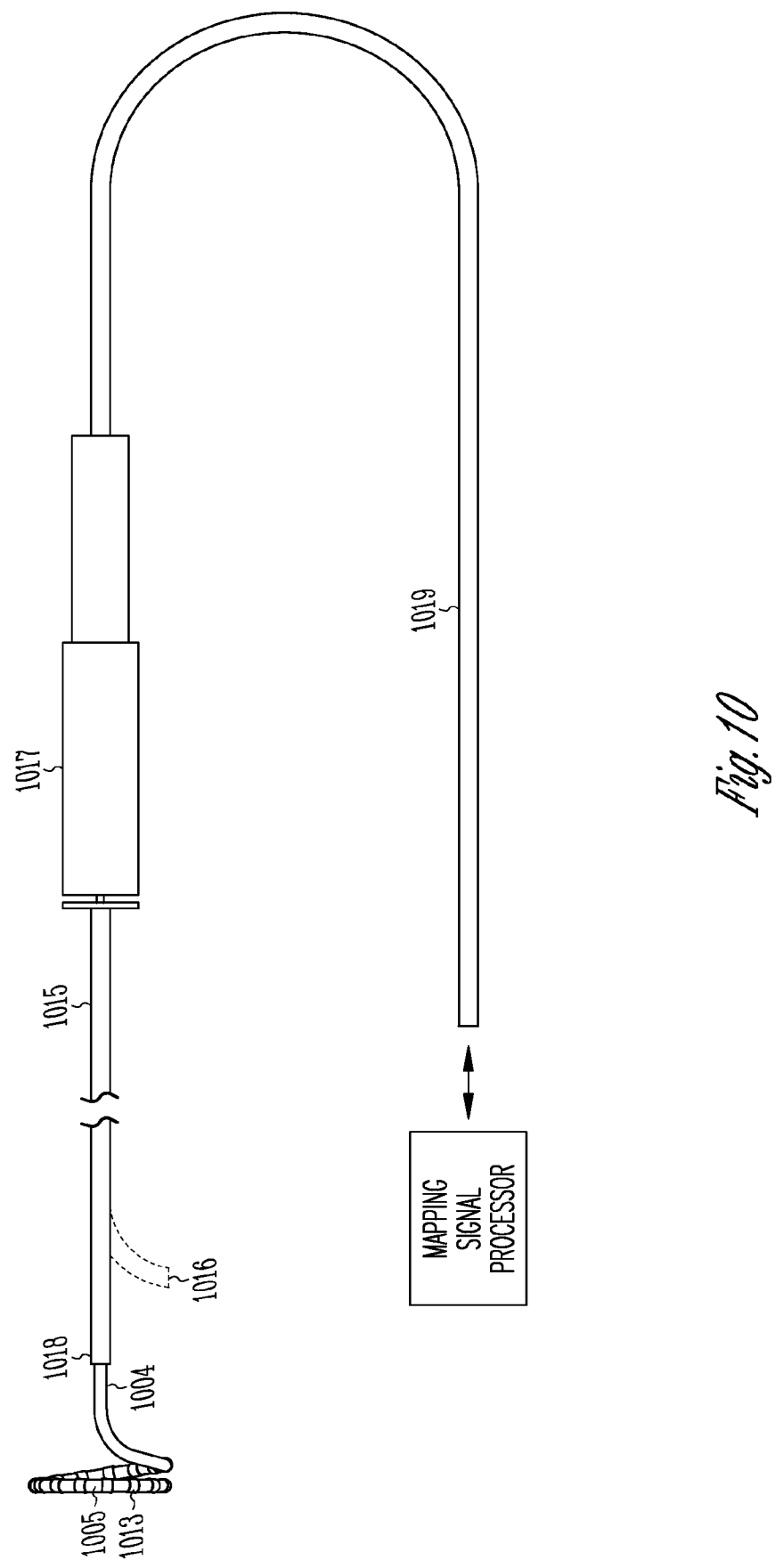
FIG. 10 illustrates a mapping catheter system embodiment.

FIG. 10 illustrates a mapping catheter system embodiment. The illustrated catheter includes the loop section 1005 with mapping electrodes 1013 to provide a probe assembly for PV mapping. Although the probe assembly is described in conjunction with pulmonary vein tissue, the probe assemblies may be used for other body tissues. Although the electrodes are described below as mapping electrodes, in alternative embodiments, the electrodes may be multi-functional electrodes used for mapping, pacing, and/or ablating body tissue.

The catheter can be functionally divided into four regions: the operative distal probe assembly region (e.g. the distal portion of catheter body 1004 and the loop section 1013), a main catheter region 1015, a deflectable catheter region 1016, and a proximal catheter handle region where a handle assembly 1017 including a handle is attached. A body of the catheter may include tubular element(s) to provide the desired functionality to the catheter. The catheter may also include a sheath 1018 that, when the probe assembly is moved proximally into the sheath, the sheath collapses the probe assembly. Moving the probe assembly out of the sheath allows the loop to be deployed.

The deflectable catheter region 1016 allows the catheter to be steered through the vasculature of the patient and allows the probe assembly to be accurately placed adjacent the targeted tissue region. A steering wire (not shown) may be slidably disposed within the catheter body. The handle assembly may include a steering member to push and pull the steering wire. Pulling the steering wire causes the wire to move proximally relative to the catheter body which, in turn, tensions the steering wire, thus pulling and bending the catheter deflectable region into an arc. Pushing the steering wire causes the steering wire to move distally relative to the catheter body which, in turn, relaxes the steering wire, thus allowing the catheter to return toward its form. To assist in the deflection of the catheter, the deflectable catheter region may be made of a lower durometer plastic than the main catheter region.

A mapping signal processor may be coupled to the catheter, allowing a physician to map the electrical activity in the target tissue site before, during and/or subsequent to the ablation process. The mapping processor is in electrical communication with the mapping electrodes 1013 via a mapping cable 1019 and the signal wires. The signal wires may be routed, through a mapping wire tubular member in the catheter body.

The following description for placing the probe assembly is provided by way of example, and not limitation. The probe assembly is in a collapsed condition when introduced into a patient's body. Placement of the catheter within the vasculature of the patient is typically facilitated with the aid of an introducer guide sheath or guide wire, which was previously inserted into the patient's vasculature, e.g., femoral vein. The introducer guide sheath is introduced into the left atrium of the heart using a conventional retrograde approach, i.e., through the respective aortic and mitral valves of the heart. One or more well-known visualization devices and techniques, e.g., ultrasound, fluoroscopy, etc., may be used to assist in navigating and directing the catheter to and from the targeted region. Alternatively, the introducer guide sheath may be introduced into the left atrium using a conventional transeptal approach, i.e., through the vena cava and atrial septum of the heart.

In either a conventional retrograde approach or transeptal approach, the catheter is introduced through the introducer guide sheath until the probe assembly resides within the left atrium. Once inside the left atrium, the physician may deliver the probe assembly into a desired pulmonary vein through rotational movement of the steering knob on the catheter handle. The physician situates the probe assembly within a selected tissue region in the interior of the pulmonary vein, adjacent to the opening into the left atrium. The probe assembly is deployed, where the sheath slides away from the probe assembly, removing the compression force thereon. When the probe assembly expands, mapping electrodes contact the pulmonary vein tissue. These mapping electrodes are used to sense electrical activity in the pulmonary vein tissue, and may be used to pace pulmonary vein tissue as well. Mapping data received and interpreted by the mapping signal processor is displayed for use by the physician to locate aberrant pulmonary vein tissue. The probe assembly may be moved one or more times, which may require collapsing and deploying the probe assembly one or more times, in an effort to locate aberrant pulmonary vein tissue.

This application is intended to cover adaptations or variations of the present subject matter. It is to be understood that the above description is intended to be illustrative, and not restrictive. The scope of the present subject matter should be determined with reference to the appended claims, along with the full scope of legal equivalents to which such claims are entitled.

What is claimed is:

1. A mapping probe assembly, comprising:
   a body frame with a lumen therein, the body frame including a catheter shaft region and a skived loop section where a portion of the body frame is removed toward the interior of the skived loop section; and
   a plurality of mapping electrodes attached around the skived loop section, wherein electrical conductors extend through the lumen of the body frame to the mapping electrodes.

2. The mapping probe assembly of claim 1, wherein the body frame is constructed from a nickel titanium alloy.

3. The mapping probe assembly of claim 1, wherein the skived loop section has a tapered distal portion.

4. The mapping probe assembly of claim 1, further comprising a control wire connected to the skived loop section, wherein pushing the control wire distally with respect to the skived loop section increases a diameter of the loop section and pulling the control wire proximally with respect to the skived loop section decreases the diameter of the loop section.

5. The mapping probe assembly of claim 1, further comprising a braided portion around a distal portion of the body frame, wherein the braided portion extends substantially around the skived loop section.

6. The mapping probe assembly of claim 5, further comprising an outer shaft portion around the braided portion, wherein the outer shaft portion has holes through which the electrical conductors extend.

7. The mapping probe assembly of claim 1, wherein the plurality of mapping electrodes includes a plurality of ring electrodes approximately equally spaced around the skived loop section.

8. The mapping probe assembly of claim 1, wherein the skived loop section has a generally planar loop and a loop center, and the catheter shaft is aligned with a line that is generally perpendicular to the planar loop and that intersects the planar loop proximate to the loop center.

9. The mapping probe assembly of claim 8, wherein the skived loop section is sized and configured to provide a generally uniform force in a radially outward direction to secure the mapping probe assembly in a pulmonary vein ostium.

10. A mapping probe assembly, comprising:
    a body frame with a lumen therein, the body frame including a catheter shaft region, a loop section, and a transition region between the catheter shaft region and the loop section;
    the loop section having a generally planar loop, and further having a loop center, wherein the loop section of the body frame is a skived portion in which a portion of the body frame toward the loop center has been removed;
    the catheter shaft having an alignment generally perpendicular to the loop section, wherein the alignment of the catheter shaft is along a line that intersects the planar loop proximate to the loop center; and
    a plurality of mapping electrodes attached around the loop section, wherein electrical conductors extend through the lumen of the body frame to the mapping electrodes.

11. The mapping probe assembly of claim 10, wherein the body frame is constructed from a nickel titanium alloy.

12. The mapping probe assembly of claim 10, wherein the loop section has a tapered distal portion.

13. The mapping probe assembly of claim 10, further comprising:
    a braided portion around a distal portion of the body frame, wherein the braided portion extends substantially around the loop section; and
    an outer shaft portion around the braided portion, wherein the outer shaft portion has holes through which the electrical conductors extend.

14. The mapping probe assembly of claim 10, wherein the plurality of mapping electrodes includes a plurality of ring electrodes approximately equally spaced around the loop section.

15. A mapping system, comprising:
    a steerable catheter with a distal end and a sheath at the end; and
    a mapping probe assembly configured to be deployed through the distal end of the steerable catheter and to collapse into the sheath of the steerable catheter, the mapping probe assembly comprising:
    a body frame with a lumen therein, the body frame including a catheter shaft region and a skived loop section where a portion of the body frame is removed toward the interior of the skived loop section, wherein in the deployed mapping probe assembly, the skived loop section has a generally planar loop and a loop center, and the catheter shaft has an alignment generally perpendicular to the loop section, wherein the alignment of the catheter shaft is along a line that intersects the planar loop proximate to the loop center; and
    a plurality of mapping electrodes attached around the skived loop section, wherein electrical conductors extend through the lumen of the body frame to the mapping electrodes.

16. The mapping system of claim 15, wherein the body frame is constructed from a nickel titanium alloy.

17. The mapping system of claim 15, wherein the skived loop section has a tapered distal portion.

18. The mapping system of claim 15, further comprising a control wire connected to the skived loop section, wherein pushing the control wire distally with respect to the skived loop section increases a diameter of the loop section and pulling the control wire proximally with respect to the skived loop section decreases the diameter of the loop section.

19. The mapping system of claim 15, further comprising:
a braided portion around a distal portion of the body frame, wherein the braided portion extends substantially around the loop section; and
an outer shaft portion around the braided portion, wherein the outer shaft portion has holes through which the electrical conductors extend.

20. The mapping system of claim 15, wherein the plurality of mapping electrodes includes a plurality of ring electrodes approximately equally spaced around the skived loop section.

21. The mapping system of claim 15, further comprising a mapping signal processor electrically connected to the mapping electrodes using the electrical conductors extending through the lumen, wherein the mapping signal processor is configured to use the plurality of mapping electrodes to map electrical activity in a targeted tissue site.

22. The mapping system of claim 15, wherein the steerable catheter is configured to deploy the probe assembly near a pulmonary vein ostium.

\* \* \* \* \*